United States Patent
Dubois

(10) Patent No.: US 8,642,792 B2
(45) Date of Patent: Feb. 4, 2014

(54) METHOD FOR THE SYNTHESIS OF OMEGA-AMINO-ALKANOIC ACIDS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 502 days.

(21) Appl. No.: 12/527,054

(22) PCT Filed: Feb. 15, 2008

(86) PCT No.: PCT/FR2008/050254
§ 371 (c)(1),
(2), (4) Date: Jan. 26, 2010

(87) PCT Pub. No.: WO2008/104722
PCT Pub. Date: Sep. 4, 2008

(65) Prior Publication Data
US 2010/0168453 A1    Jul. 1, 2010

(30) Foreign Application Priority Data

Feb. 15, 2007    (FR) ..................................... 07 53285

(51) Int. Cl.
*C07C 227/00*    (2006.01)
*C07C 229/00*    (2006.01)

(52) U.S. Cl.
USPC ............................. 554/114; 560/155; 562/553

(58) Field of Classification Search
None
See application file for complete search history.

(56) References Cited

U.S. PATENT DOCUMENTS

| | | | | |
|---|---|---|---|---|
| 2,327,119 A | * | 8/1943 | Martin ........................... | 562/553 |
| 2,674,607 A | * | 4/1954 | Genas ........................... | 554/114 |
| 3,026,342 A | * | 3/1962 | Wust ............................. | 554/114 |
| 3,244,733 A | * | 4/1966 | Wakasa et al. ................ | 554/114 |
| 3,354,203 A | * | 11/1967 | Little ............................. | 554/114 |

FOREIGN PATENT DOCUMENTS

WO    WO 03/093215    11/2003

OTHER PUBLICATIONS

Green, J.L. et al., 13-aminotridecanoic acid from erucic acid, 1969, I & E Product Research and Development, vol. 8, No. 2, pp. 171-176.*
Gaumann, T. et al., Infrared spectra of omega-amino acids, 1952, Helvetica Chimica Accta, vol. 35, No. 5, pp. 53-60.*
Gaumann, T. et al., Infrared spectra of omega-amino acids, 1952, Helvetica Chimica Accta, vol. 35, No. 5, (1 page abstract).*
Schaverien, C.J. et al., A Well-Characterized, Highly Active, Lewis Acid Free Olefin Metathesis Catalyst, J.Am.Chem.Soc., 108, pp. 2771-2771, 1986.
Couturier, J-L. et al., A Cyclometalated Aryloxy(chloro)neopentylidene-tungsten Complex: A Highly Active and Stereoeslective Catalyst for the Metathesis of cis- and trans-2-Pentene, Norbornene, 1-Methyl-norbornene, and Ethyl Oleate, Angew. Chem. Int. Ed. Engl., 31,No. 5, pp. 628-631, 1992.
Schwab, P. et al., A Series of Well-Defined Metathesis Catalysts-Synthesis of [RuC12(=CHR')(PR3)2] and its Reactions, Angew .Chem. Int. Ed. Engl., 34,No. 18, pp. 2039-2041, 1995.
Scholl, M. et al., Snythesis and Activity of a New Generation of Ruthenium-Based Olefin Metathesis Catalyst Coordinated with 1,3-Dimesityl]-4,5-dihydroimidazol-2-ylidene Ligands, Organic Letters, American Chemical Society, vol. 1, No. 6, pp. 953-956, 1999.
Mol, J., Application of olefin metathesis in oleochemistry: and example of green chemistry, Green Chemistry, Royal Chemical Society, vol. 4, pp. 5-13, 2002.
Cotara, L. et al., Efficient and Scaleable Methods of omega-Functionalized Nonanoic Acids: Development of Novel Process for Azelaic and 9-Aminononanoic Acids, Organic Process Research and Development, vol. 5, No. 1, pp. 69-76, 2001.
Ayorinde, F.O. et al., Systhesis of 12-Aminododecanoic and 11-Aminoundecanoic Acids from Vernolic Acid, JAOCS, vol. 74, No. 5, pp. 531-538, 1997.
Kohlhase, W.L. et al. 9-Aminononanamide and Nylon-9 From Azelaaldehydic Derivatives of Soybean Oil, JAOCS, vol. 47, pp. 193-188, 1970.
Holmes, R.L. et al., Preparation of Dodecylamine adn 6-Aminohexanoic Acid from Petroselinic Acid, JAOC, vol. 39, pp. 411-414, 1963S, No. 9, 1962.
Miller W.K. et al., Nylon-9 Via 9-Aminononanaic Acid from Soybean Oil, Ind. Eng. Chem. Chem. Prod. Res. Develop., vol. 10, No. 4, pp. 442-447, 1971.

* cited by examiner

*Primary Examiner* — Yate K Cutliff
(74) *Attorney, Agent, or Firm* — Smith, Gambrell & Russell, LLP

(57) ABSTRACT

The invention relates to a method for the synthesis of amino acids/esters of general formula $NH_2$—$(CH_2)_n$—COOR in which n is an integer between 5 and 14, and R is either H or an alkyl radical including from 1 to 4 carbon atoms, from natural long-chain mono-unsaturated fatty acids or esters including at least 10 adjacent carbon atoms per molecule, said method comprising: first converting, if necessary, said natural long-chain fatty acid or ester into a monounsaturated fatty acid/ester of general formula $R_1$—$(CH_2)_m$—CH=CH—$(CH_2)_p$—COOR in which $R_1$ is H, $CH_3$ or a COOR radical, m is an integer between 0 and 14 and p is an integer between 2 and 11, then submitting the latter to a crossed catalytic metathesis reaction with a compound of formula $R_2$—CH=CH—$R_3$ in which $R_2$ is either H or CN and $R_3$ is CN or $CH_2NH_2$, provided that if $R_2$ is CN, $R_3$ can be only CN, and finally converting the resulting product of the general formula $R_3$—CH=CH—$(CH_2)_p$—COOR into an amino-acid, either by hydrogenation, or by hydrogenation of the triple terminal bond, or by amination of the double terminal bond.

12 Claims, No Drawings

METHOD FOR THE SYNTHESIS OF OMEGA-AMINO-ALKANOIC ACIDS

FIELD OF THE INVENTION

The invention is directed toward a process for synthesizing ω-aminoalkanoic acids or esters of these acids from natural fatty acids, comprising at least one step of metathesis of a monounsaturated fatty acid.

BACKGROUND OF THE INVENTION

The current evolution in environmental matters is leading in the fields of energy and chemistry toward favoring the exploitation of natural raw materials originating from a renewable source.

An example of an industrial process using a fatty acid as starting material to is that of the manufacture, starting from ricinoleic acid extracted from castor oil, of 11-aminoundecanoic acid, which is the basis for the synthesis of RILSAN®. This process is described in the book "Les Procédés de Pétrochimie" by A. Chauvel et al. published by Editions TECHNIP (1986). 11-Aminoundecanoic acid is obtained in several steps. The first consists of a methanolysis of castor oil in basic medium, producing methyl ricinoleate, which is then subjected to a pyrolysis to obtain, on the one hand, heptanaldehyde and, on the other hand, methyl undecylenate. The latter product is converted into acid form by hydrolysis. The acid formed is then subjected to a hydrobromination to give the ω-bromo acid, which is converted via amination into 11-aminoundecanoic acid.

The literature contains very few documents describing the synthesis of compounds of amino acid type from natural fatty acids. Beyond the reference cited above, the Encyclopedia of Chemical Technology, 4th Edition, John Wiley & Sons, (1996) Volume 19, page 501, discloses a synthetic route for the production of a "Nylon-13" obtained by polymerization of a lactam obtained from erucic acid produced, for example, from rapeseed. This synthetic route proceeds via an oxidation, for example via ozonolysis, to produce a diacid containing 13 carbon atoms, brassylic acid. After a series of chemical transformations, the lactam 13 may be prepared from brassylic acid. The lactam 13 is then polymerized in the same manner as the lactam 12, which itself has been obtained hitherto from petroleum derivatives. This polyamide containing 13 carbon atoms appears to have properties similar to those of the polyamides 11 and 12.

The process for synthesizing 11-aminoundecanoic acid that has been performed industrially for several decades is satisfactory on the whole. However, it presents a certain number of drawbacks. The first drawback is that its implementation is in practice governed by access to a specific raw material, castor oil. Furthermore, castor oil contains a toxin: ricin, which is extremely toxic and which it is necessary to remove. The second drawback is associated with the reagents used, in particular ammonia and bromine, which require expensive precautions for storage and use. The process co-produces not only glycerol, but also many by-products that have to be upgraded separately: heptanaldehyde, esterol (mixture of untracked fatty acid esters).

Moreover, it is important to have available processes for synthesizing the entire range of long-chain ω-amino acids that may be used in industry, and especially in the polymer industry.

The problem is thus that of finding a process for the synthesis of long-chain ω-amino acids from very widely available, and thus inexpensive, renewable raw materials, which is simple to perform while at the same time avoiding the environmental constraints mentioned previously.

DETAILED DESCRIPTION OF THE INVENTION

The proposed solution consists in working starting with monounsaturated long-chain natural fatty acids. The term "long-chain natural fatty acid" means an acid obtained from plant or animal media, including algae, more generally from the plant kingdom, and which is thus renewable, containing at least 10 and preferably at least 14 carbon atoms per molecule.

Examples of such acids that may be mentioned include the C10 acids obtusilic acid (cis-4-decenoic acid) and caproleic acid (cis-9-decenoic acid), the C12 acids lauroleic acid (cis-5-dodecenoic acid) and linderic acid (cis-4-dodecenoic acid), the C14 acids myristoleic acid (cis-9-tetradecenoic acid), physeteric acid (cis-5-tetradecenoic acid) and tsuzuic acid (cis-4-tetradecenoic acid), the C16 acid palmitoleic acid (cis-9-hexadecenoic acid), the C18 acids oleic acid (cis-9-octadecenoic acid), elaidic acid (trans-9-octadecenoic acid), petroselinic acid (cis-6-octadecenoic acid), vaccenic acid (cis-11-octadecenoic acid) and ricinoleic acid (12-hydroxy-cis-9-octadecenoic acid), the C20 acids gadoleic acid (cis-9-eicosenoic acid), gondoic acid (cis-11-eicosenoic acid), cis-5-eicosenoic acid and lesquerolic acid (14-hydroxy-cis-11-eicosenoic acid), and the C22 acids cetoleic acid (cis-1'-docosenoic acid) and erucic acid (cis-13-docosenoic acid).

These various acids are obtained from plant oils extracted from various plants such as sunflower, rape, castor bean, lesquerella, olive, soybean, palm, coriander, celery, dill, carrot, fennel or *Limnanthes alba* (meadowfoam).

They are also obtained from the terrestrial or marine animal kingdom, and in the latter case, in the form either of fish, mammals or algae. They are generally fats originating from ruminants, fish such as cod, or marine mammals such as whales or dolphins.

The invention is directed toward a process for synthesizing amino acids or amino esters of general formula

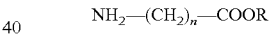
$NH_2—(CH_2)_n—COOR$ in which n represents an integer between 5 and 14, and R is either H or an alkyl radical containing from 1 to 4 carbon atoms, from monounsaturated long-chain natural fatty acids or esters containing at least 10 adjacent carbon atoms per molecule, which consists first in converting, in an optional first step, said long-chain natural fatty acid or ester, via a physical treatment, via homometathesis or via a microbiological fermentation process, into a monounsaturated fatty acid or ester of general formula

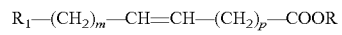
$R_1—(CH_2)_m—CH=CH—(CH_2)_p—COOR$ in which $R_1$ represents H, $CH_3$ or a radical COOR, m is an integer between 0 and 14 and p is an integer between 2 and 11, and then in subjecting said monounsaturated fatty acid or ester of general formula $R_1—(CH_2)_m—CH=CH—(CH_2)_p—COOR$ to a catalytic cross-metathesis reaction with a compound of formula $R_2—CH=CH—R_3$ in which $R_2$ is either H or CN and $R_3$ is H, CN or $CH_2NH_2$, with the proviso that if $R_2$ is CN, $R_3$ can be only H or CN, and then finally in converting into an ω-amino acid the resulting product corresponding to the general formula $R_3—CH=CH—(CH_2)_p—COOR$, either by hydrogenation of the terminal triple bond, or by amination of the terminal double bond.

Depending on the starting materials and on the amino acid to be synthesized, this process may include a preliminary step for forming the monounsaturated fatty acid or ester of general formula $R_1—(CH_2)_m—CH=CH—(CH_2)_p—COOR$.

This optional preliminary first step may be a simple physical separation via any means known to those skilled in the art for purifying the charge. It may also be a pyrolysis of the natural fatty acid/ester allowing the production of an ω-amino acid whose chain length is shorter than the natural fatty acid/ester via consecutive reactions. It may also be a chemical reaction of homometathesis type not involving co-reagents. Finally, it may be a biological fermentation allowing the long-chain natural fatty acids/esters to be converted into diacid (diester) form.

In the process of the invention, the fatty acid may be treated either in its acid form or in its ester form. Conversion from one form to the other, via methanolysis, esterification or hydrolysis, which is entirely trivial, does not constitute a chemical transformation within the meaning of the process.

The process of the invention is especially directed toward the synthesis of 11-aminoundecanoic acid from oleic acid. It consists, in a first step, in reacting, in the presence of a metathesis catalyst, oleic acid with methacrylonitrile of formula $CN-CH=CH_2$, and then, in a second step, in subjecting the product resulting from the first step of formula $CN-CH=CH-(CH_2)_7-COOH$ to a hydrogenation to produce 11-aminoundecanoic acid.

All the mechanisms detailed below illustrate, to facilitate the description, the synthesis of the acids. However, metathesis is also effective with an ester, and for that matter even more effective, since the medium is generally more anhydrous. Similarly, the schemes illustrate reactions with the cis isomer of the acids (or esters); the mechanisms are just as applicable to the trans isomers.

Optionally, the methyl ester of 11-aminoundecanoic acid may be polymerized into polyamides, with the release of methanol.

The reaction process is as follows:

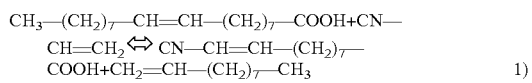  1)

During the process, the reaction below may take place:

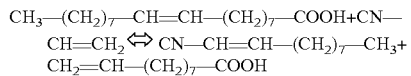

However, after consecutive reaction with the methacrylonitrile present in the medium, the formation of $CN-CH=CH-(CH_2)_7-COOH$ will always be obtained according to

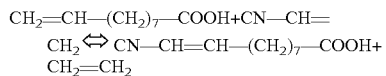

with formation of an olefin comprising the nitrite function.

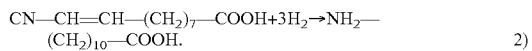  2)

In this embodiment of the process, it is unnecessary to perform a preliminary step since oleic acid is in a sufficient degree of purity.

It should be noted that 10-aminodecanoic acid may also be obtained via this process. Specifically, by orienting the reaction toward the process

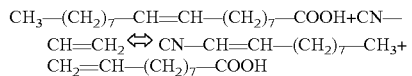

and by working with a deficit of acrylonitrile, the 9-decenoic acid may be treated by hydrobromination and amination, to synthesize 10-aminodecanoic acid.

In one variant of the process, the C18 fatty acid in its diacid form may be used for the cross-metathesis reaction. In this case, during a preliminary step, oleic acid either is converted into diacid via homometathesis of the oleic acid, or is converted into diacid via fermentation.

The reaction process is then the following:

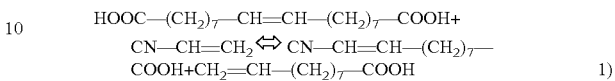  1)

and via consecutive reaction with acrylonitrile:

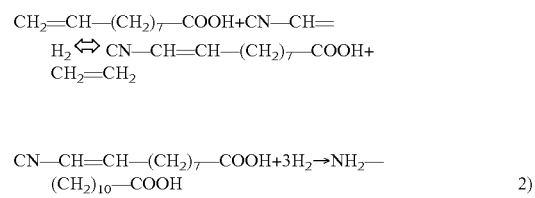

$$CN-CH=CH-(CH_2)_7-COOH+3H_2 \rightarrow NH_2-(CH_2)_{10}-COOH \quad 2)$$

It may be observed that, during the reaction, 9-decenoic acid is formed, which, itself also, if the process is performed with an excess of acrylonitrile, will lead to the formation, via cross metathesis with acrylonitrile, of the compound of formula $CN-CH=CH-(CH_2)_7-COOH$, which also leads after hydrogenation to 11-aminoundecanoic acid with production of ethylene. An important advantage of the process is thus the absence of co-product, apart from the ethylene, which is easily removed.

The reaction mechanism for this reaction is illustrated by scheme 1 below:

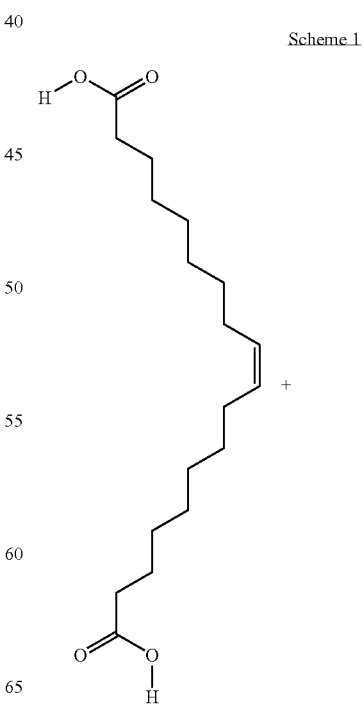

Scheme 1

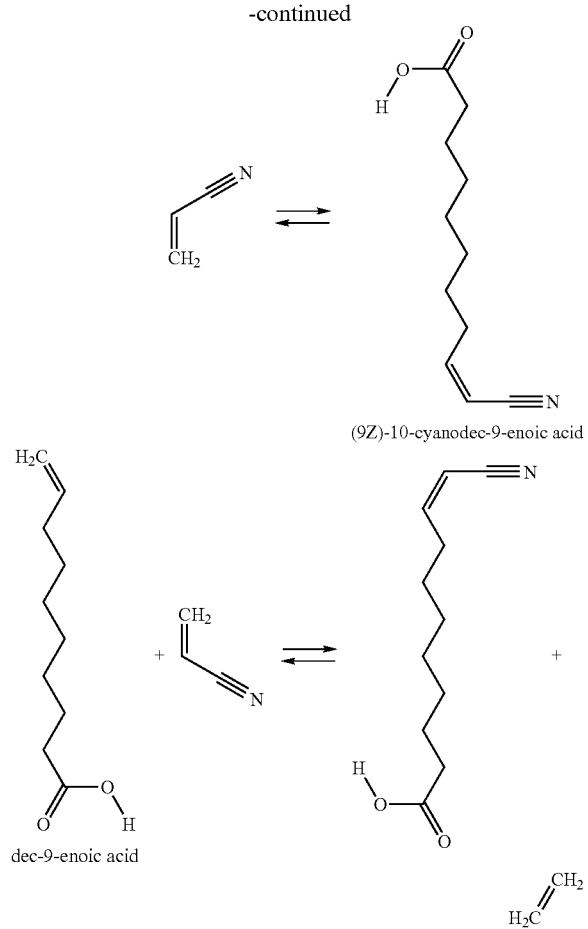

(9Z)-10-cyanodec-9-enoic acid dec-9-enoic acid

In another variant of the process using dinitrile (2-butenedinitrile) as cross-metathesis co-reagent, two CN—CH=CH—(CH$_2$)$_7$—COOH molecules may be obtained directly without co-product, which appreciably improves the efficiency of the process.

The reaction process with 2-butenedinitrile is then as follows:

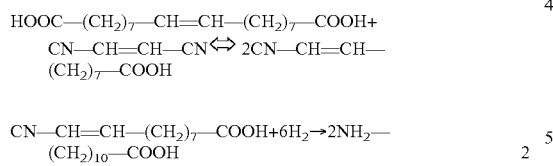

As may be observed, the process of the invention allows the synthesis of diacid from a single molecule of C18 acid, in fact two molecules of C11 acid precursor of 11-aminoundecanoic acid, this being possible irrespective of the nitrile, acrylonitrile or dinitrile reagent used. It is clear that this specificity gives the process an important economic advantage; specifically, it avoids having to is worry about upgrading the usual reaction co-products, for example heptanal and/or derivatives thereof, in the industrial process via pyrolysis of ricinoleic acid.

For the synthesis of 8-aminooctanoic acid, petroselinic acid (cis-6-octadecenedioic acid) may be used as natural fatty acid starting material. Assuming that this acid is of sufficient purity, it is subjected to a cross metathesis with acrylonitrile and the product obtained from this reaction is then hydrogenated.

The reaction mechanism for this reaction is as follows:

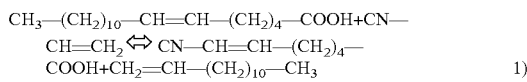

During the process, the reaction below may take place:

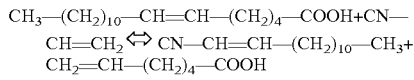

However, after consecutive reaction with the methacrylonitrile present in the medium, the formation of CN—CH=CH—(CH$_2$)$_4$—COON will still be obtained according to

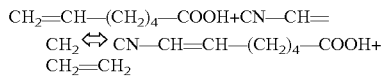

with formation of an olefin comprising the nitrile function.

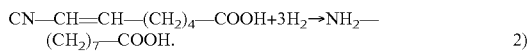

For the synthesis of 7-aminoheptanoic acid, petroselinic acid (cis-6-octadecenedioic acid) may be used as natural fatty acid starting material. Assuming that this acid is of sufficient purity, it is subjected to a cross metathesis with ethylene (ethenolysis), and an amination of the terminal double bond of the intermediate heptenoic acid is then performed.

The reaction mechanism for this reaction is as follows:

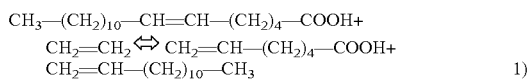

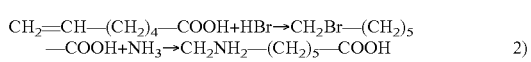

The reaction mechanism for the first step of this reaction is illustrated by scheme 2 below.

Scheme 2

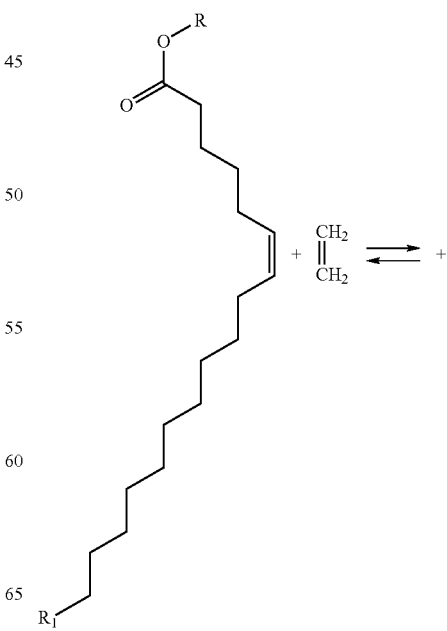

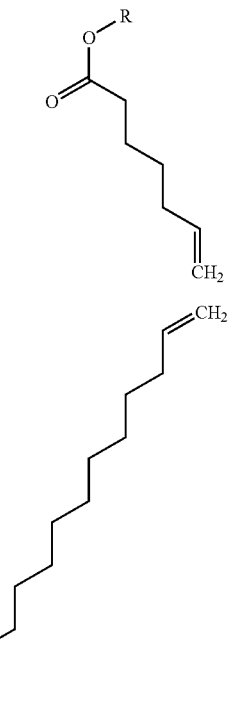

It may be observed that it is also possible to obtain 8-aminooctanoic acid from the heptenoic acid obtained from the above first step by performing a cross metathesis with acrylonitrile.

For the synthesis of 12-aminododecanoic acid, ricinoleic acid may be used as fatty acid starting material. This acid, in its methyl ester form, is first subjected to a thermal pyrolysis as preliminary step, and the acid fraction, after hydrolysis of the ester, obtained from this pyrolysis is subjected to a cross metathesis with acrylonitrile and is then hydrogenated.

The simplified scheme of the reaction process is then as follows:

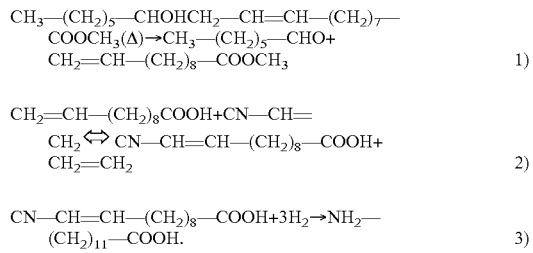

For the synthesis of 12-aminododecanoic acid from ricinoleic acid, acrylonitrile may be replaced in the cross-metathesis reaction with allylamine CH$_2$=CH—CH$_2$NH$_2$.

The reaction scheme then becomes:

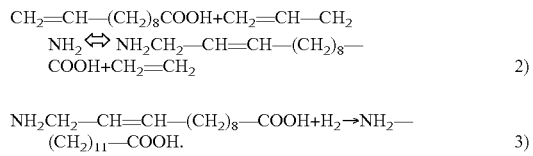

For the synthesis of 14-aminotetradecanoic acid, lesquerolic acid may be used as natural fatty acid starting material. Lesquerolic acid, of sufficient purity, is subjected, in its methyl ester form, first to a preliminary step of pyrolysis, and the acid fraction, after hydrolysis of the ester, obtained from this pyrolysis is subjected to a cross metathesis with acetonitrile and is then hydrogenated.

The reaction process is as follows:

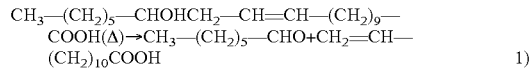

For the synthesis of 15-aminopentadecanoic acid, erucic acid may be used as natural fatty acid starting material. This acid, of sufficient purity, is subjected to a cross metathesis with acetonitrile (or dinitrile) and the acid fraction is then hydrogenated.

The reaction process is as follows:

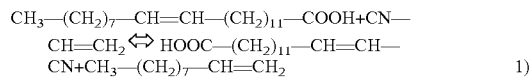

in the course of the process, the following reaction may take place:

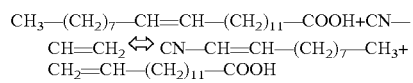

However, after consecutive reaction with the methacrylonitrile present in the medium, the formation of CN—CH=CH—(CH$_2$)$_{11}$—COOH is still obtained according to

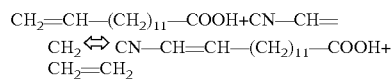

with formation of an olefin comprising the nitrile function.

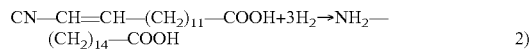

It may also be envisioned to perform, prior to the cross metathesis, a homometathesis of erucic acid.

The reaction process is as follows:

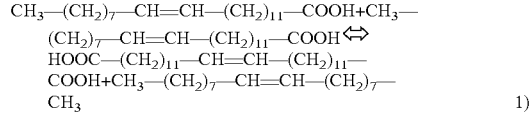

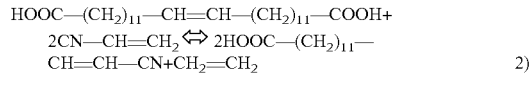

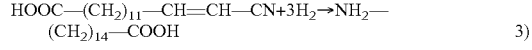

Starting with erucic acid, it is also possible to obtain 14-aminotetradecanoic acid by performing a first step of cross metathesis with ethylene, which makes it possible to obtain 13-tetradecenoic acid, which may then be aminated according to the process described above.

For the synthesis of 7-aminoheptanoic acid, cis-5-eicosenoic acid may be used as starting material.

The reaction mechanism is as follows:

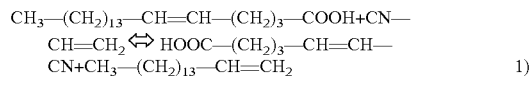

In the course of the process, the following reaction may take place:

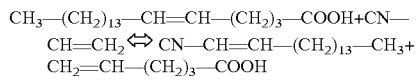

However, after consecutive reaction with the methacrylonitrile present in the medium, the formation of CN—CH=CH—(CH$_2$)$_3$—COOH will still be obtained according to

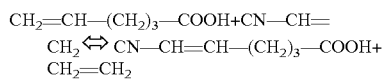

with formation of an olefin comprising the nitrile function.

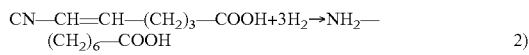

Metathesis reactions have been known for a long time, although their industrial applications are relatively limited. As regards their use in the conversion of fatty acids (esters), reference may be made to the article by J. C. Mol "Catalytic metathesis of unsaturated fatty acid esters and oil" published in Topics in Catalysis Vol. 27, Nos. 1-4, February 2004 (Plenum Publishing Corporation).

Catalysis of the metathesis reaction has been the subject of numerous studies and development of sophisticated catalytic systems. Examples that may be mentioned include the tungsten complexes developed by Schrock et al. (J. Am. Chem. Soc. 108 (1986) 2771 or Basset et al Angew. Chem., Engl. Ed., 31 (1992) 628. More recently, catalysts known as Grubbs catalysts have appeared (Grubbs et al., Angew. Chem., Engl. Ed., 34 (1995) 2039 and Organic Lett. 1 (1999) 953), which are ruthenium-benzylidene complexes. This is a case of homogeneous catalysis. Heterogeneous catalysts have also been developed, based on metals such as rhenium, molybdenum and tungsten deposited on alumina or silica. Finally, studies have been performed for the production of immobilized catalysts, i.e. catalysts whose active principle is that of the homogeneous catalyst, especially ruthenium-carbene complexes, but which is immobilized on an inactive support. The object of these studies is to increase the selectivity of the reaction with respect to parasite reactions such as "homometathesis" between the reagents placed in contact. They act not only on the structure of the catalysts, but also on the incidence of the reaction medium and the additives that may be introduced.

In the process of the invention, any active and selective metathesis catalyst may be used. However, ruthenium-based catalysts will preferably be used.

The metathesis reaction of the first step is performed at a temperature of between 20 and 100° C.

After the first step, the undecylenic acid nitrile is separated from the medium, for example by distillation, to subject this nitrile to a hydrogenation.

The invention also relates to one or more amino acids or amino esters of renewable origin of general formula NH$_2$—(CH$_2$)$_n$—COOR in which n represents an integer between 5 and 14, and R is either H or an alkyl radical containing from 1 to 4 carbon atoms.

The term "amino acids or amino esters of renewable origin" means amino is acids or amino esters that comprise carbon of renewable origin.

Specifically, unlike materials derived from fossil matter, materials partly composed of renewable raw materials contain $^{14}C$. All carbon samples taken from living organisms (animals or plants) are in fact a mixture of three isotopes: $^{12}C$ (representing ~98.892%), $^{13}C$ (~1.108%) and $^{14}C$ (traces: 1.1×10$^{-10}$%). The $^{14}C/^{12}C$ ratio of living tissues is identical to that of the atmosphere. In the environment, $^{14}C$ exists in two predominant forms: in mineral form, i.e. carbon dioxide (CO$_2$) and in organic form, i.e. carbon incorporated into organic molecules.

In a living organism, the $^{14}C/^{12}C$ ratio is kept constant by the metabolism since the carbon is continually exchanged with the environment. As the proportion of $^{14}C$ is substantially constant in the atmosphere, this is likewise the case in the organism, for as long as it is alive, since it absorbs this $^{14}C$ just as it absorbs $^{12}C$. The mean $^{14}C/^{12}C$ ratio is equal to 1.2×10$^{-12}$.

$^{12}C$ is stable, i.e. the number of $^{12}C$ atoms in a given sample is constant over time. $^{14}C$, on the other hand, is radioactive (each gram of carbon from a living being contains enough $^{14}C$ isotope to give 13.6 disintegrations per minute) and the number of such atoms in a sample decreases over time (t) according to the law:

$$n = no \exp(-at)$$

in which:
no is the number of $^{14}C$ at origin (at the death of the creature, animal or plant),
n is the number of $^{14}C$ atoms remaining after a time t,
a is the disintegration constant (or radioactive constant); it is related to the half-life.

The half-life (or period) is the time after which any particular number of radioactive nuclei or of unstable particles of a given species is reduced by half by disintegration; the half-life T½ is related to the disintegration constant a by the formula aT½=ln 2. The half-life of $^{14}C$ is 5730 years.

Taking into account the half-life (T½) of $^{14}C$, it is considered that the content of $^{14}C$ is constant from the extraction of the plant raw materials up to the manufacture of the amino acid or amino ester, and even up to the end of its use.

The Applicant considers that an amino acid or amino ester is partly derived from renewable starting materials if it contains at least 20% by mass of C of renewable origin out of the total mass of carbon, and preferably at least 50% by mass of C of renewable origin out of the total mass of carbon.

In other words, an amino acid or amino ester is derived from renewable raw materials if it contains at least 0.2×10$^{-10}$% by mass of $^{14}C$ and preferably 0.6×10$^{-10}$% by mass of $^{14}C$.

At the present time, there are at least two different techniques for measuring the $^{14}C$ content of a sample:
by liquid scintillation spectrometry: This method consists in counting the beta particles produced by the disintegration of $^{14}C$. The beta radiation produced by a sample of known mass (known number of $^{12}C$ atoms) over a certain time is counted. This radioactivity is proportional to the number of $^{14}C$ atoms, which may thus be determined. The $^{14}C$ present in the sample emits β radiation, which, on contact with a scintillation liquid (scintillant), generates photons. These photons have different energies (between 0 and 156 Kev) and form what is known as a $^{14}C$ spectrum. According to two variants of this method, the analysis is performed either on the CO$_2$ produced beforehand by the carbon sample in a suitable absorbent solution, or on benzene after preliminary conversion of the carbon sample into benzene.
by mass spectrometry: The sample is reduced to graphite or gaseous CO$_2$, and analyzed in a mass spectrometer. This technique uses an accelerator and a mass spectrometer to separate the $^{14}C$ ions from the $^{12}C$ ions and thus determine the ratio of the two isotopes.

All these methods for measuring the $^{14}C$ content of materials are precisely described in the standards ASTM D 6866 (especially D6866-06) and in the standards ASTM D 7026 (especially 7026-04).

The measuring method preferentially used in the case of the amino acids or amino esters of the invention is mass spectrometry described in the standard ASTM D6866-06 (accelerator mass spectroscopy).

The invention is illustrated by the nonlimiting examples that follow.

Example 1

The bispyridine ruthenium complex catalyst (8) described in the publication by Chen-Xi Bai et al., Tetrahedron Letters, 46 (2005) 7225-7228 is used. The synthesis is performed in $CH_2Cl_2$, at a concentration of 0.05 M of reagent, at a temperature of 45° C., and for 12 hours. The yields are determined by chromatographic analysis. In the present case, the reagent is the diacid HOOC—$(CH_2)_7$—CH=CH—$(CH_2)_7$—COOH, and 4 equivalents of acrylonitrile are used (4 mol of acrylonitrile per mole of diacid), and with a catalyst concentration of 5 mol %. The yield of acid nitrile CN—CH=CH—$(CH_2)_7$—COOH is 50%.

Example 2

The ruthenium complex catalyst (3) described in the publication by Stefan Randl et al., Synlett (2001) 10, 430 is used. This compound is very stable and does not decompose when it is exposed to air or water. The synthesis is performed in $CH_2Cl_2$, at a concentration of 0.05 M of reagent, at a temperature of 45° C., and for 2 hours. The yields are determined by chromatographic analysis. In the present case, the reagent is 10-undecenoic acid and 2 equivalents of acrylonitrile are used (2 mol of acrylonitrile per mole of acid) and with a catalyst concentration of 5 mol %. The yield of acid nitrile CN—CH=CH—$(CH_2)_8$—COON is 67%.

Example 3

The bispyridine ruthenium complex catalyst (8) described in the publication by Chen-Xi Bai et al., Org. Biomol. Chem., (2005), 3, 4139-4142 is used. The synthesis is performed in $CH_2Cl_2$, at a concentration of 0.05 M of reagent, at a temperature of 45° C., and for 12 hours. The yields are determined by chromatographic analysis. In the present case, the reagent is a diester $CH_3OOC$—$(CH_2)_7$—CH=CH—$(CH_2)_7$—$COOCH_3$, and 2 equivalents of acrylonitrile are used (3 mol of acrylonitrile per mole of diester), and with a catalyst concentration of 10 mol % relative to the reagent. The yield of nitrile ester CN—CH=CH—$(CH_2)_7$—$COOCH_3$ is 70%.

Example 4

Methyl Undecenoate/Acrylonitrile Cross Metathesis 100 mg of methyl 10-undecenoate (0.5 mmol), 53 mg of acrylonitrile (1 mmol) and 10 ml of toluene distilled over sodium-benzophenone are placed in a 50 ml Schlenk tube. 1.5 mg ($2.4\times10^{-3}$ mmol) of second-generation Hoveyda-Grubbs catalyst ((1,3-bis(2,4,6-trimethylphenyl)-2-imidazolidinylidene)dichloro(o-iso-propoxyphenylmethylene)ruthenium, available from Aldrich) are added. The mixture is heated to 100° C. and left to react for 1 hour under nitrogen and with magnetic stirring. The reaction mixture is analyzed by gas chromatography (dodecane standard). The conversion of the methyl 10-undecenoate is 94%. The selectivity toward methyl 11-cyano-10-undecenoate (cis+trans mixture) is 100%. The TON (turnover number) is 188.

Example 5

Methyl Undecenoate/Acrylonitrile Cross Metathesis with Continuous Addition of Catalyst 100 mg of methyl 10-undecenoate (0.5 mmol), 53 mg of acrylonitrile (1 mmol) and 8 ml of toluene distilled over sodium-benzophenone are placed in a 50 ml second-generation Hoveyda-Grubbs catalyst dissolved in 2 ml of toluene is added, using a syringe and a syringe press, over a period of 2 hours 40 minutes, under nitrogen and with magnetic stirring. At the end of the addition, the mixture is left to react for 1 hour at 80° C. The reaction mixture is analyzed by gas chromatography (dodecane standard). The conversion of the methyl 10-undecenoate is 94%. The selectivity toward methyl 11-cyano-10-undecenoate (cis+trans mixture) is 100%. The TON is 940.

Example 6

Unsaturated $C_{18}$ Diester/Acrylonitrile Cross Metathesis 170 mg of methyl 9-octadecenedioate (0.5 mmol), 106 mg of acrylonitrile (2 mmol) and 10 ml of toluene distilled over sodium-benzophenone are placed in a 50 ml Schlenk tube. 3 mg ($5\times10^{-3}$ mmol) of second-generation Hoveyda-Grubbs catalyst are added. The mixture is heated to 100° C. and left to react for 1 hour under nitrogen and with magnetic stirring. The reaction mixture is is analyzed by gas chromatography (tetradecane standard). The conversion of the unsaturated diester is 95%. The selectivity toward methyl 10-cyano-9-decenoate (cis+trans mixture) is 93% (with 7% selectivity toward methyl 9-decenoate). The TON is 95.

Example 7

Unsaturated $C_{18}$ Diester/Acrylonitrile Cross Metathesis with Continuous Addition of Catalyst 170 mg of methyl 9-octadecenedioate (0.5 mmol), 106 mg of acrylonitrile (2 mmol) and 8 ml of toluene distilled over sodium-benzophenone are placed in a 50 ml Schlenk tube. The mixture is heated to 80° C., and 0.6 mg ($10^{-3}$ mmol) of second-generation Hoveyda-Grubbs catalyst dissolved in 2 ml of toluene is then added, using a syringe and a syringe press, over a period of 4 hours, under nitrogen and with magnetic stirring. At the end of the addition, the mixture is left to react at 80° C. for 1 hour. The reaction mixture is analyzed by gas chromatography (tetradecane standard). The conversion of the unsaturated diester is 98%. The selectivity toward methyl 10-cyano-9-decenoate (cis+trans mixture) is 96% (with 4% selectivity toward methyl 9-decenoate). The TON is 490.

The invention claimed is:
1. A process for synthesizing amino acids or amino esters of general formula $NH_2$—$(CH_2)_n$—COOR in which n represents an integer between 5 and 14, R is either H or an alkyl radical containing from 1 to 4 carbon atoms, and containing at least $0.2\times10^{-10}$% by mass of $^{14}C$, from monounsaturated long-chain natural fatty acids or esters containing at least 10 adjacent carbon atoms per molecule, which consists first in converting, in an optional first step, said long-chain natural fatty acid or ester, via a physical treatment, via homometathesis or via a microbiological fermentation process, into a monounsaturated fatty acid or ester of general formula $R_1$—$(CH_2)_m$—CH=CH—$(CH_2)_p$—COOR in which $R_1$ represents H, $CH_3$ or a radical COOR, m is an integer between 0 and 14 and p is an integer between 2 and 11, and then subjecting said monounsaturated fatty acid or ester of general formula $R_1$—$(CH_2)_m$—CH=CH—$(CH_2)_p$—COOR to a catalytic cross-metathesis reaction with a compound of formula $R_2$—CH=CH—$R_3$ in which $R_2$ is either H or CN and R3 is H, CN or $CH_2NH_2$, with the proviso that if $R_2$ is CN, $R_3$ can be only CN, and finally converting the resulting product corresponding to the general formula R3-CH=CH—$(CH_2)_p$—COOR, into an ω-amino acid by hydrogenation or by amination.

2. The process as claimed in claim 1, wherein the synthesized monounsaturated fatty acid or ester of general formula $R_1$—$(CH_2)_m$—CH=CH—$(CH_2)_p$—COOR is subjected to a metathesis reaction with acrylonitrile, and is then subjected to a hydrogenation.

3. The process as claimed in claim 2, wherein an amino acid of formula $NH_2$—$(CH_2)_{10}$—COOH is synthesized by reacting acrylonitrile with oleic acid, followed by a hydrogenation of an intermediate compound of formula CN—CH=CH—$(CH_2)_7$—COOH.

4. The process as claimed in claim 3, wherein the amino acid of formula $NH_2$—$(CH_2)_{10}$—COOH is synthesized by reacting an excess of acrylonitrile with an oleic diacid of formula HOOC—$(CH_2)_7$—CH=CH—$(CH_2)_7$—COOH, followed by a hydrogenation of an intermediate compound of formula CN—CH=CH—$(CH_2)_7$—COOH.

5. The process as claimed in claim 1, wherein an amino acid of formula $NH_2$—$(CH_2)$10-COON is synthesized by reacting a 2-butenedinitrile of formula CN—CH=CH—CN with an oleic diacid of formula HOOC—$(CH_2)_7$—CH=CH—$(CH_2)_7$—COOH, followed by a hydrogenation of an intermediate compound of formula CN—CH=CH—$(CH_2)_7$—COOH.

6. The process as claimed in claim 2, wherein an amino acid of formula $NH_2$—$(CH_2)_7$—COOH is prepared from petroselinic acid, which is subjected to metathesis with acrylonitrile, the intermediate acid of formula CN—CH=CH—$(CH_2)_4$—COOH then being hydrogenated.

7. The process as claimed in claim 2, wherein an amino acid of formula $NH_2$—$(CH_2)_{11}$—COOH is prepared from an acid of formula $CH_2$=CH—$(CH_2)_8$COOH obtained from pyrolysis of ricinoleic acid, via metathesis with acrylonitrile, and is then subjected to a hydrogenation.

8. The process as claimed in claim 2, wherein an amino acid of formula $NH_2$—$(CH_2)_{13}$—COOH is prepared from the acid of formula $CH_2$=CH—$(CH_2)_{10}$COOH, obtained, from pyrolysis of lesquerolic acid, via metathesis with acrylonitrile, and is then subjected to a hydrogenation.

9. The process as claimed in claim 2, wherein an amino acid of formula $NH_2$—$(CH_2)_6$—COOH is prepared from cis-5-eicosenoic acid via metathesis with acrylonitrile, followed by hydrogenation.

10. The process as claimed in claim 2, wherein an amino acid of formula $NH_2$—$(CH_2)_{14}$—COOH is prepared from erucic acid via metathesis with acrylonitrile, followed by hydrogenation.

11. The process as claimed in claim 1, wherein an amino acid of formula $NH_2$—$(CH_2)_{11}$—COOH is prepared from an acid of formula $CH_2$=CH—$(CH_2)_8$COOH obtained, from pyrolysis of ricinoleic acid, via metathesis with allylamine, and is then subjected to a hydrogenation.

12. An amino acid or amino ester of general formula $NH_2$—$(CH_2)_n$—COOR in which n represents an integer between 5 and 14, and R is either H or an alkyl radical containing from 1 to 4 carbon atoms made by the process of claim 1, wherein the amino acid or amino ester contains at least $0.2 \times 10^{-10}$% by mass of $^{14}C$.

* * * * *